US012660989B2

(12) United States Patent
Ballentine et al.

(10) Patent No.: US 12,660,989 B2
(45) Date of Patent: Jun. 23, 2026

(54) LARYNGOSCOPE AND OCCLUSION APPARATUS

(71) Applicants:Austin Joseph Ballentine, Dayton, OH (US); Lauren Mackenzie Edmonson, Ogden, UT (US); Timothy Lee Norman, Jamestown, OH (US); Caleb Talbot Williams, Charlotte, NC (US); Jeffrey Scott Williams, Durango, CO (US)

(72) Inventors: Austin Joseph Ballentine, Dayton, OH (US); Lauren Mackenzie Edmonson, Ogden, UT (US); Timothy Lee Norman, Jamestown, OH (US); Caleb Talbot Williams, Charlotte, NC (US); Jeffrey Scott Williams, Durango, CO (US)

( * ) Notice: Subject to any disclaimer, the term of this patent is extended or adjusted under 35 U.S.C. 154(b) by 742 days.

(21) Appl. No.: 17/852,437

(22) Filed: Jun. 29, 2022

(65) Prior Publication Data

US 2022/0409025 A1 Dec. 29, 2022

Related U.S. Application Data

(60) Provisional application No. 63/216,099, filed on Jun. 29, 2021.

(51) Int. Cl.
*A61B 1/267* (2006.01)
*A61B 1/00* (2006.01)
*A61B 1/06* (2006.01)

(52) U.S. Cl.
CPC ............ *A61B 1/00147* (2013.01); *A61B 1/06* (2013.01); *A61B 1/267* (2013.01)

(58) Field of Classification Search
CPC .......... A61B 1/267–2676; A61B 17/132–1355
See application file for complete search history.

(56) References Cited

U.S. PATENT DOCUMENTS

| | | | | |
|---|---|---|---|---|
| 3,884,240 A | * | 5/1975 | Gilman ................ | A61B 17/132 2/209 |
| 5,304,201 A | * | 4/1994 | Rice ..................... | A61B 17/132 606/151 |
| 2006/0095073 A1 | * | 5/2006 | Beto ....................... | A61B 90/50 606/201 |
| 2008/0262479 A1 | * | 10/2008 | Barela ..................... | A61B 5/01 606/1 |

(Continued)

FOREIGN PATENT DOCUMENTS

| | | | | | |
|---|---|---|---|---|---|
| EP | 2679145 A1 | * | 1/2014 | ......... | A61B 1/00128 |

OTHER PUBLICATIONS

"Combat Ready Clamp", Combat Medical, Harrisburg, NC 28075, http://combatmedicalsystems.com.

*Primary Examiner* — Eduardo C Robert
*Assistant Examiner* — Steven J Cotroneo
(74) *Attorney, Agent, or Firm* — HILL, KERTSCHER & WHARTON, LLP; Gregory T. Ourada

(57) ABSTRACT

This application discloses embodiments for a device contemplated for use by combat medics and first responders for rapid treatment of Zone 2 penetrating neck injuries. The device incorporates a support arm and an occlusion arm featuring an occluding head which is applied to the wound. In certain embodiments, the support arm is in the form of a detachable neck support which attaches to a laryngoscope blade.

6 Claims, 9 Drawing Sheets

(56) References Cited

U.S. PATENT DOCUMENTS

| 2012/0031400 | A1* | 2/2012 | Shimm | .............. | A61M 16/00 |
| | | | | | 128/200.26 |
| 2013/0072913 | A1* | 3/2013 | Yi | .............. | A61B 1/00133 |
| | | | | | 606/1 |
| 2015/0087918 | A1* | 3/2015 | Vasan | .............. | A61B 90/16 |
| | | | | | 600/215 |
| 2016/0066925 | A1* | 3/2016 | van Sparrentak | .... | A61B 17/132 |
| | | | | | 606/203 |
| 2019/0314027 | A1* | 10/2019 | Clark | .............. | A61B 17/128 |
| 2021/0059688 | A1* | 3/2021 | Rajebi | .............. | A61B 5/0053 |

* cited by examiner

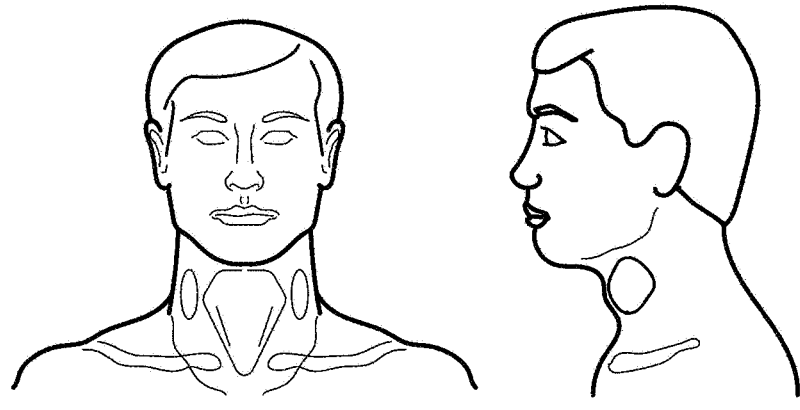
FIG. 11A        FIG. 11B
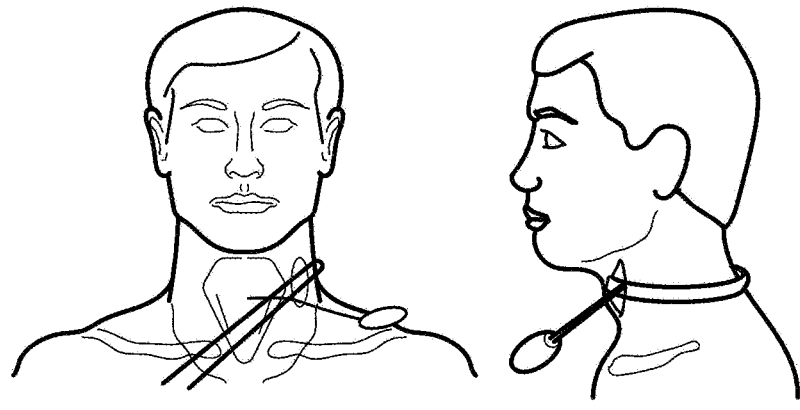
FIG. 11C        FIG. 11D

LARYNGOSCOPE AND OCCLUSION APPARATUS

CROSS REFERENCE TO RELATED APPLICATIONS

This application claims priority to provisional Appl. Ser. No. 63/216,099 filed Jun. 29, 2021, the contents of which are incorporated herein in their entirety.

BACKGROUND

It is well-known that the sooner an injured person can be transported to a medical facility—ideally within the "golden hour" from the time of injury—the higher the likelihood of survival. First responders—whether civilian paramedics or military medics/corpsmen—are therefore in need of devices which facilitate quick stabilization of injuries so that injured persons can be rapidly transported to a trauma treatment facility.

There is a particularly urgent need for treatment options for penetrating injuries in Zone 2 of the neck, as well as methods and equipment for rapidly stabilizing such injuries. For clinical purposes, when referencing trauma treatment of neck injuries, the neck is divided into three zones. Zone 1 is the area between the clavicles and the cricoid cartilage. This zone contains vital structures which include the innominate vessels, the origin of the common carotid artery, the subclavian vessels and the vertebral artery, the brachial plexus, the trachea, the esophagus, the apex of the lung, and the thoracic duct. Zone 2 is the area between the cricoid cartilage and the angle of the mandible. The carotid and vertebral arteries, the internal jugular veins, the trachea, and the esophagus are located in Zone 2. This zone has comparatively easy access for clinical examination and surgical exploration. Zone 2 is the largest zone and the most commonly injured in the neck. Zone 3 is the area between the angle of the mandible and the base of the skull. This area contains the distal carotid and vertebral arteries and the pharynx. [1]

[1] "Neck Trauma", Titilola Alao and Muhammad Waseem, http://www.ncbi.nlm.nih.gov/books/NBK470422, accessed May 27, 2022

Zone 2 of the neck is of particular interest due to the lack of protection in that area when considering military body armor and the significant structures it contains. Prior to the conception of the device disclosed herein, the only solution for arresting bleeding from penetrating Zone 2 arterial neck injuries was for a first responder to manually apply pressure to the wound with their hands, and to maintain this pressure until the patient was transported to a medical facility where surgical repair of the wound could be effected. While tourniquets are usually preferred to control arterial bleeding in the field, traditional tourniquets are obviously inappropriate for use on the neck as they will either cause strangulation or cut off blood flow to both sides of the brain. Therefore, a first responder must maintain manual pressure on the artery until the patient arrives at a medical facility where the wound can be surgically treated. This results in a first responder's hands being occupied at the neck so that they are unable to provide additional support for other injuries or people.

An existing mechanical occlusion applicator that may be used as a last resort in Zone 2 penetrating neck injuries is the CroC® "Combat Ready Clamp" by Combat Medical Systems, LLC of Fayetteville, NC, as shown in FIG. 1. However, this device is primarily intended for use in the inguinal, axillary, and proximal iliac areas, and has severe operational and physical limitations when used for Zone 2 trauma.

Accordingly, there is a need for a device designed for use by first responders which can precisely halt bleeding from the carotid artery after a penetrating Zone 2 neck injury while preserving blood flow to the brain and the patient's airway. Such a device would dramatically increase the survivability of such injuries. The device would allow the responder to stabilize the injured person on-scene as well as allow the responder to do other lifesaving functions simultaneously and maintain pressure to the neck during transport to the treating medical facility. Such a device is ideally lightweight, portable and easy to apply, since it is envisioned that the device will be employed by not only civilian paramedics, but also military personnel under combat conditions. In addition to controlling bleeding while stabilizing an injured trauma patient, first responders may need to establish a definitive airway to a patient in the field. First responders employ a conventional laryngoscope to intubate such a patient to facilitate resuscitation. A laryngoscope is a common device carried by first responders and combat medic personnel to facilitate the establishment of definitive airways via intubation using an endotracheal tube. Since many first responders, particularly military medics and corpsmen, have limited space and strict weight limitations for medical equipment, a device which has multiple capabilities (e.g. intubation and occlusion of bleeding) will be highly valued.

SUMMARY

This disclosure describes a variety of embodiments of a device specially designed to apply precise pressure to the common carotid artery and internal jugular vein for the purpose of tamponading blood-flow without the constant intervention and attention of medical personnel. These embodiments may be used for all zones of the neck. Certain embodiments of the device feature a laryngoscope used to facilitate endotracheal intubation that is incorporated into the neck support of the device. These embodiments are dual purpose: they can be used for endotracheal intubation as well as for stopping blood flow from an neck wound.

Preferred embodiments of the device disclosed herein have two primary components, a support arm and an occluding arm. The support arm encircles a patient's neck generally opposite from a neck wound, while the occluding arm provides support for an adjustable, interchangeable occluding head, which applies direct pressure to a neck wound. The occluding arm slides back and forth relative to the support arm. In one embodiment, the support arm and the occluding arm feature a "T" shaped channel having ratcheting teeth permitting the support arm to translate linearly relatively to the occluding arm in one direction, while preventing linear translation in the opposite direction. Thus, the occluding arm can be rapidly moved toward the support arm and locked into the desired position. Typically, such sliding adjustment of the support arm and the occluding arm will be enough to occlude the bleeding. However, the occluding arm further incorporates a fine adjustment knob to allow the position of the occluding head to be adjusted to increase occlusion pressure if needed in transport, or if the proper occlusion can't be achieved by adjusting the support and occlusion arms of the device relative to one another.

Additionally, the overall shape of the support arm, with certain modifications to the basic embodiment described above, allows the occlusion device to function as a laryngoscope. The shape of the lower limb of the support arm in certain embodiments is formed in the shape of a laryngoscope blade. In one such embodiment, the blade is a conventional Mackintosh (e.g. MAC3) laryngoscope blade. Such dual-use embodiments feature a detachable neck support having a channel accommodating the laryngoscope blade so that the neck support essentially snaps into place over the laryngoscope blade.

DESCRIPTION OF THE DRAWINGS

FIGS. 11A-11D illustrate an alternate embodiment of the device featuring inflatable occlusion heads.

DETAILED DESCRIPTION OF PREFERRED EMBODIMENTS

Figure 1:
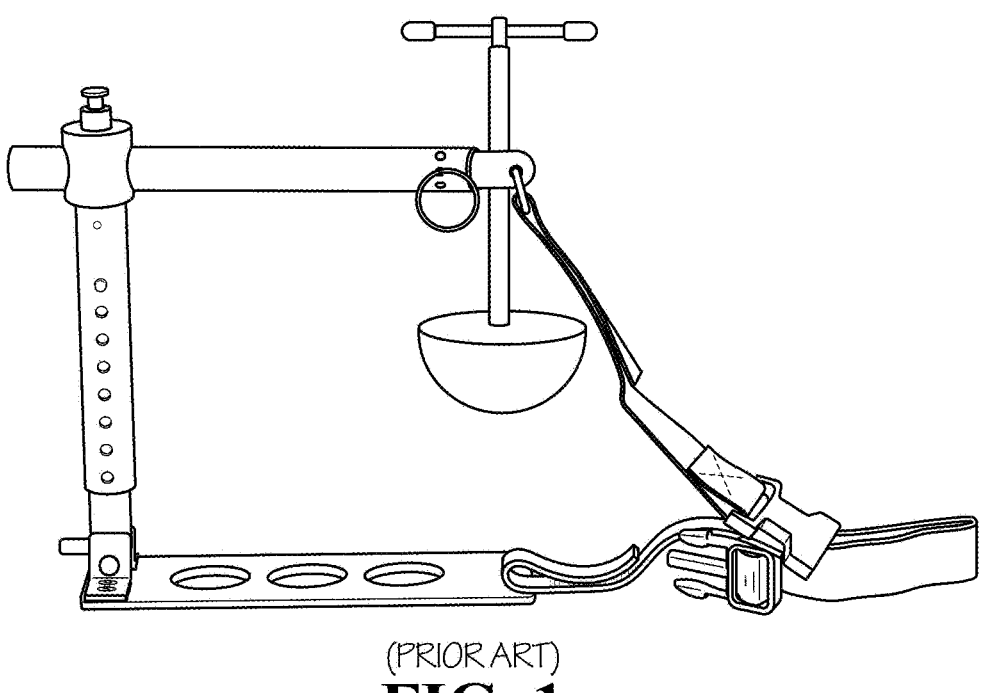
FIG. 1 is an illustration of a prior art mechanical occlusion applicator.
Figure 2:
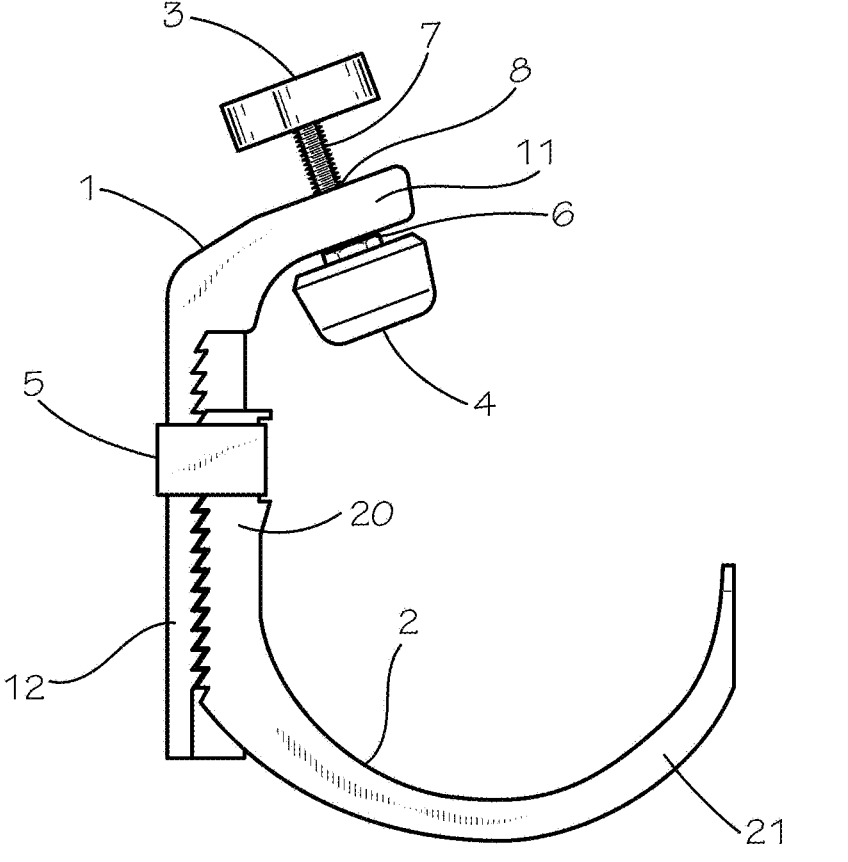
FIG. 2 illustrates one preferred embodiment of the device for treatment of bleeding from a Zone 2 neck wound.

FIG. 2 illustrates a preferred embodiment of the occlusion device. This embodiment occludes blood flow to the carotid artery on one side of the neck, while leaving the carotid artery patent on the other side of the neck. The carotid arteries feed into the Circle of Willis, which is a vascular arrangement that allows redundant blood flow to the brain. Thus, as long as one carotid artery is patent, blood flow to the brain may be maintained.

Figure 8:
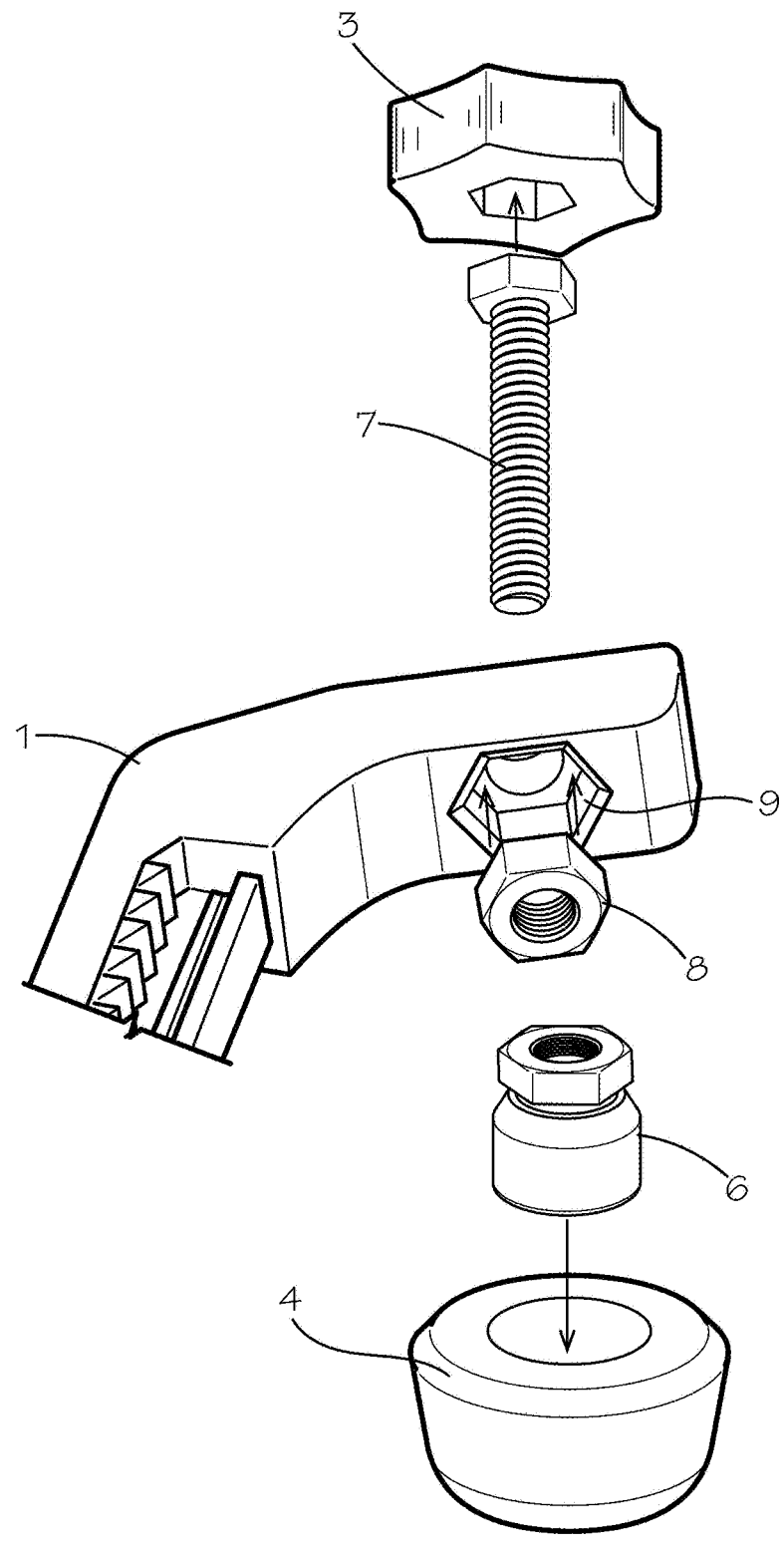
FIG. 8 illustrates the installation of the occlusion head in the upper limb of the occlusion arm for a preferred embodiment.

The embodiment illustrated in FIG. 2 consists of occluding arm 1, support arm 2, fine adjustment knob 3, occluding head 4, fastening strap 5, swiveling tip 6, adjustment screw 7, and adjustment nut 8. An exploded view of the upper limb of the occluding arm 1 is shown in FIG. 8.

Figure 7:
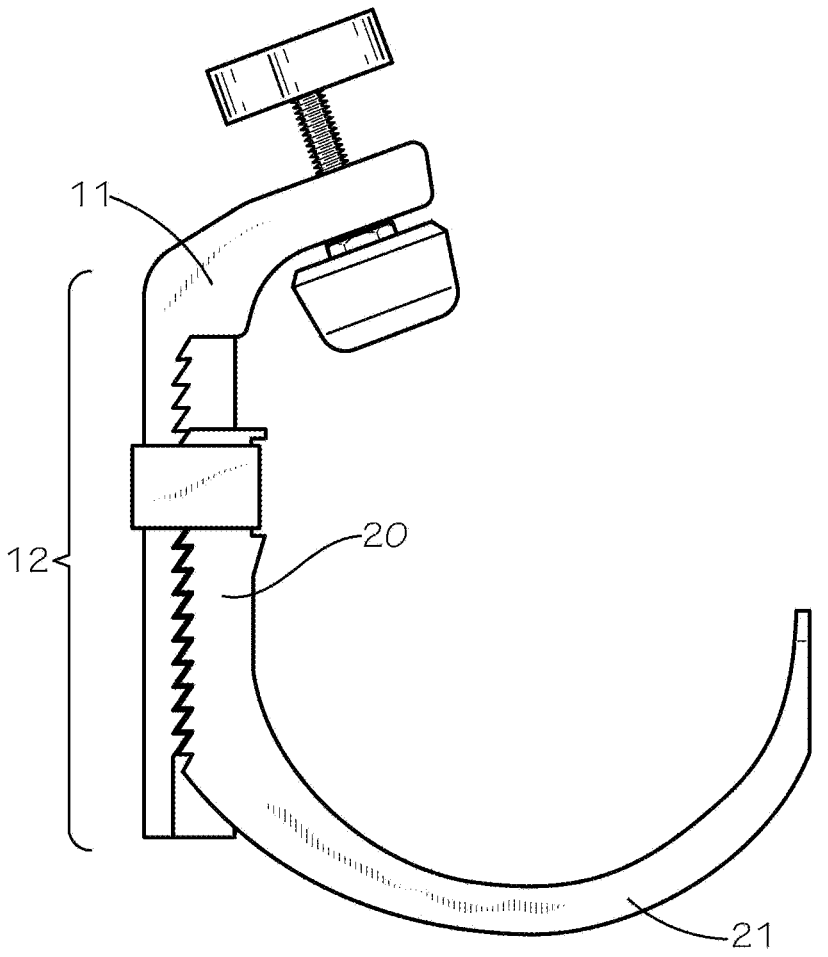
FIG. 7 illustrates the angular disposition of the upper limb of the occlusion arm relative to the lower limb in a preferred embodiment.

Occluding arm 1 features an upper limb 11, which is disposed at an encounter angle relative to a lower limb 12. Similarly, reference to support arm 2 includes straight support arm upper limb 20, and curved support arm lower limb 21. The encounter angle is typically 20 degrees elevated from the anterior plane as illustrated in FIG. 7. Experimental use of the occlusion device in cadaverial tests revealed that satisfactory arterial occlusion occurred when the angle of the occluding arm upper limb relative to the anterior plane was approximately 20 degrees. The angle between the occluding arm upper limb 11 and occluding arm lower limb 12 gives a resultant co-linear force by the occluding head 4 between the support arm 2 and occluding arm 1 so that there is no net torque on the occlusion device.

Figure 3:
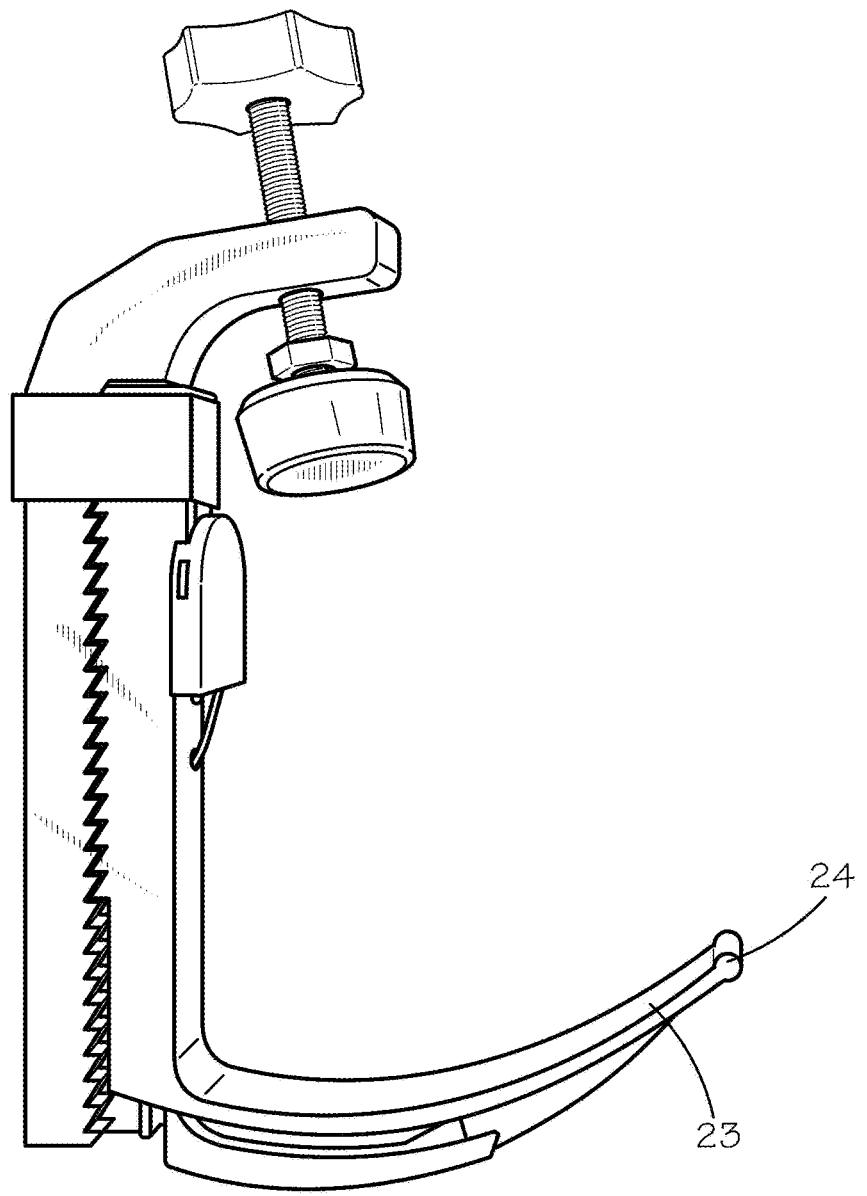
FIG. 3 illustrates a second embodiment of the device featuring a laryngoscope blade incorporated into the support arm.
Figure 4:
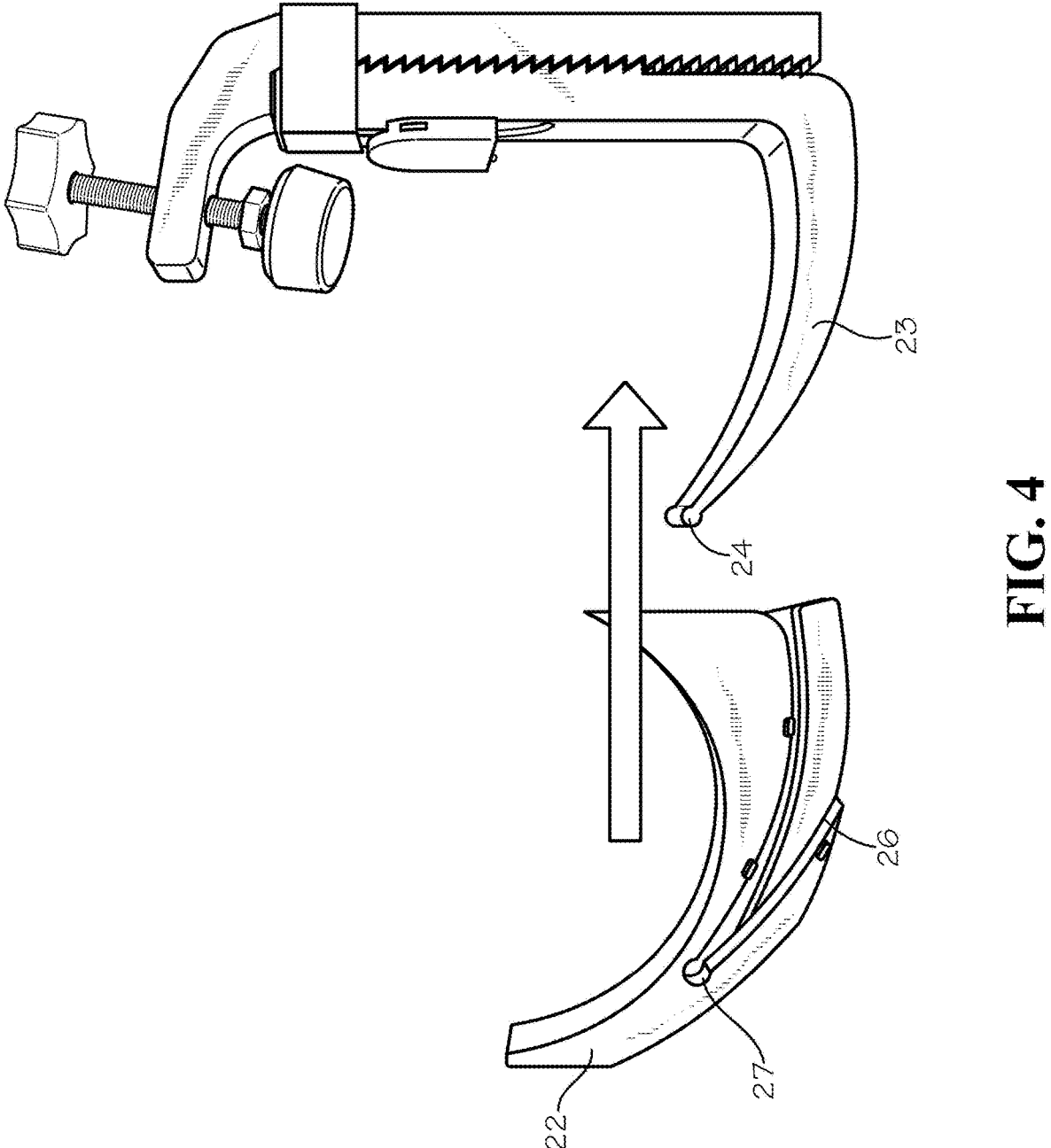
FIG. 4 illustrates an embodiment of a device having a detachable neck support and the laryngoscope blade of the support arm.
Figure 5:
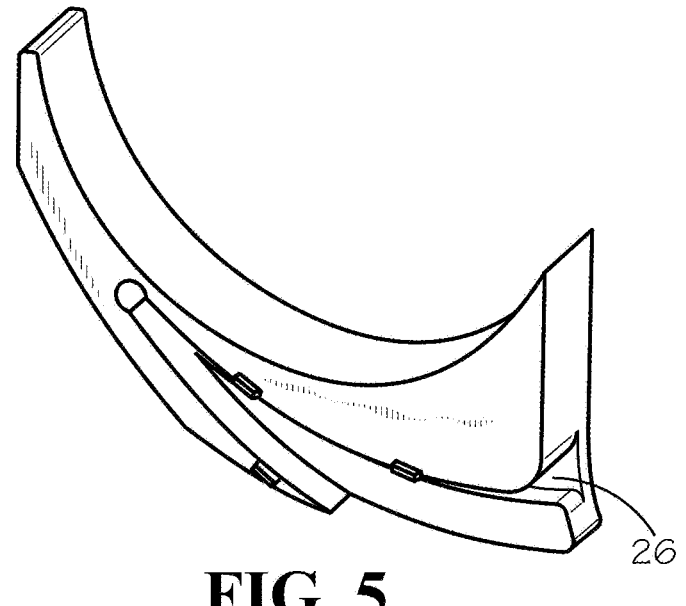
FIG. 5 illustrates the detachable neck support and its channel for the laryngoscope blade.

An alternate embodiment of the device is illustrated in FIG. 3. The support arm lower limb 21 in this embodiment is in the shape of a laryngoscope blade 23. In one embodiment, laryngoscope blade 23 is a conventional Mackintosh (e.g. MAC3) laryngoscope blade. Detachable neck support 22 incorporates a channel 26 that accommodates the insertion of laryngoscope blade 23 as illustrated in FIGS. 4 and 5. Channel 26 incorporates a cylindrical locking cavity 27 which engages the cylindrical tip 24 of laryngoscope blade 23. This allows detachable neck support 22 to "snap onto" laryngoscope blade 23. Thus, certain embodiments of the occlusion device may be quickly converted for use as a laryngoscope. As mentioned above, a device having a dual-use capability is valuable to first responder personnel, particularly combat medics and corpsman for whom space is at a premium and weight strictly limited.

Figure 6:
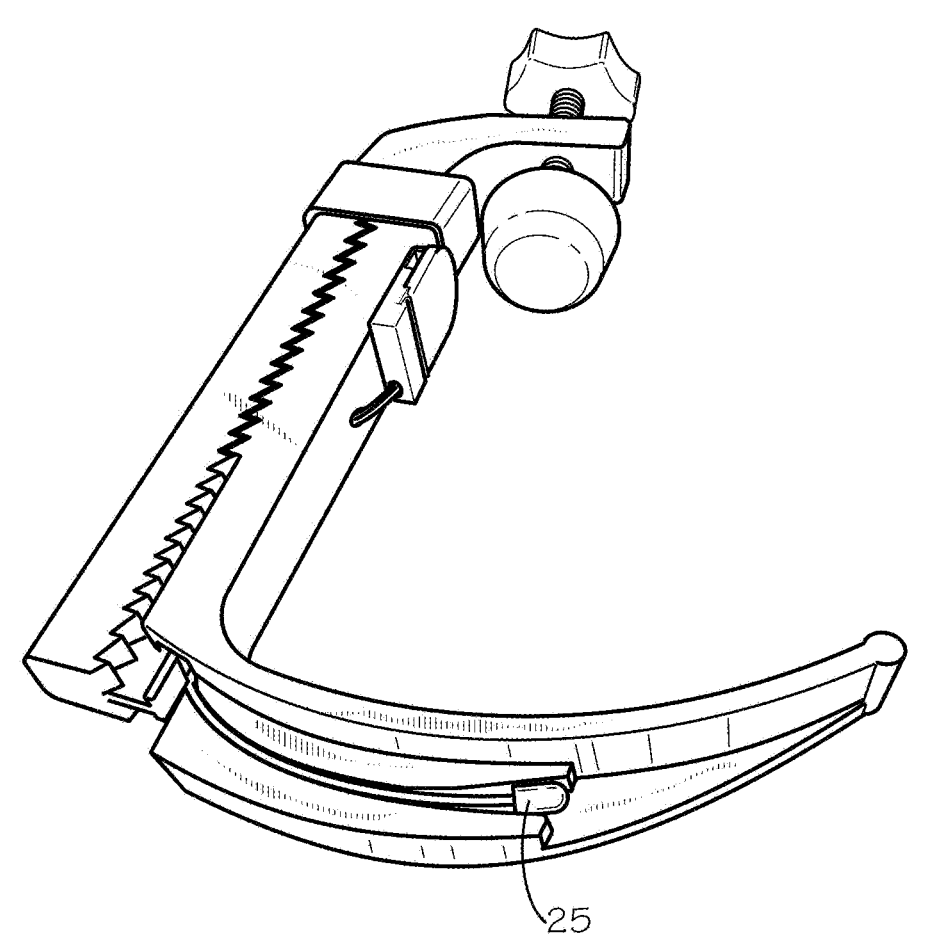
FIG. 6 illustrates a light incorporated into the laryngoscope blade.

Laryngoscope blades 23 typically incorporate a light 25 on one side of the blade to facilitate its insertion into a patient's airway, as illustrated in FIG. 6. This light should be compact and intense, so in the preferred embodiments, battery powered LED lights, fiber optic lights, and the like can be employed. In embodiments featuring a laryngoscope blade having a light, the battery or other power source for light 25 would typically be disposed in the upper limb of support arm 20.

Occluding arm 1 is capable of rapidly being moved linearly relative to support arm 2 and locked into place. To this end, preferred embodiments feature a ratcheting track which allows occluding arm 1 and support arm 2 to be moved relative to each other so that occluding head 4 can be positioned with the neck support 2 in place. The ratcheting locking system is accomplished in preferred embodiments using a "T" shaped track system. This allows the user to rapidly move the occluding head 4 onto the wound, while keeping the occluding arm 1 and support arm 2 together. The user then moves the occluding arm 1 on to the patient's neck and pushes it in until the bleeding stops. FIGS. 2-4, and 6-8 show how the combination of the T-shaped track and the locking teeth allows the device to be rapidly adjusted and locked in place. Locking teeth in the occluding arm lower limb 12 engage locking teeth in the support arm upper limb 20. These teeth are shaped as shown in FIG. 7 so that linear movement of the occluding arm 1 relative to support arm 2 in one direction is allowed, while preventing movement in the opposite direction.

Figure 9:
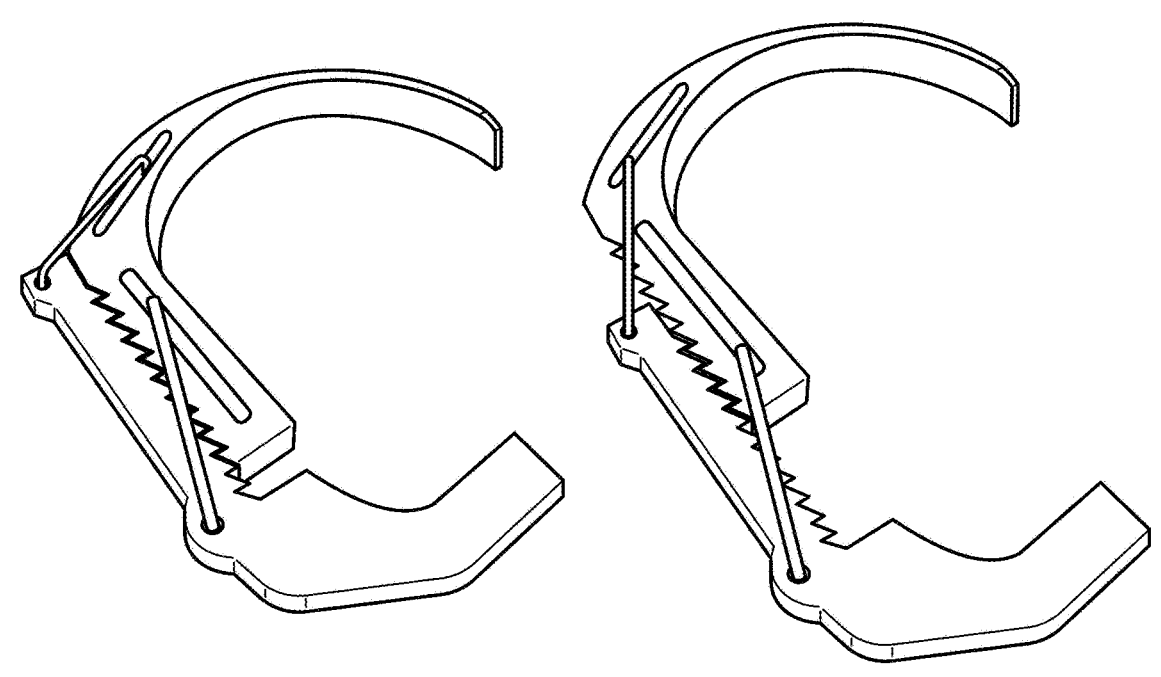
FIG. 9 illustrates an alternative embodiment of the occlusion apparatus quick application mechanism.
Figure 10:
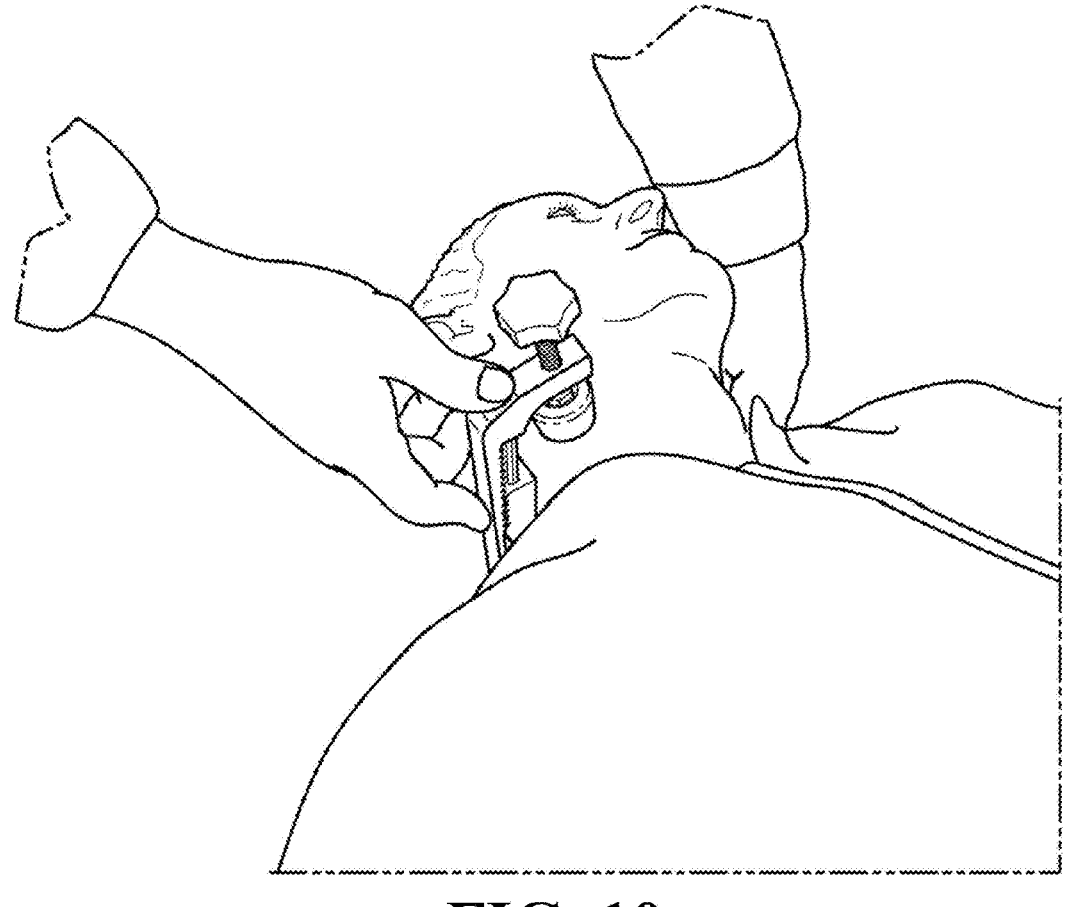
FIG. 10 illustrates application of the device to a patient in the field.

FIG. 10 shows application of the device in a training situation. The device is typically stored and carried in the collapsed form illustrated in FIG. 2, with fastening strap 5 in place around the occluding arm lower limb 12 and support arm upper limb 20. The purpose of fastening strap 5 is to hold occluding arm lower limb 12 and support arm upper limb 20 together so that the locking teeth are engaged. Conversely, in order to unlock the device, fastening strap 5 is removed or loosened so that occluding arm lower limb 12 and support arm upper limb 20 can be separated laterally so that the locking teeth are no longer engaged, although the t-shaped rail (part of occluding arm lower limb 12 in a preferred embodiment) is retained within a channel incorporated into support arm upper limb 20. Fastening strap 5 can be made of any suitable material, although preferred embodiments feature a fabric or leather strap with buckles or hook-and-loop material. An alternative embodiment illustrated in FIG. 9 involves the employment of two pivoting retaining rods attached to the occluding arm 1 which slide in grooves on the support arm 2 for quick deployment and stability.

To employ the device fastening strap 5 is removed, allowing occluding arm 1 and support arm 2 to be separated laterally so that the locking teeth disengage. In some cases, however, it is desirable to separate occluding arm 1 from support arm 2 entirely to treat an arterial neck wound. In this

6 molded out of engineered polymers, such as, but not limited to, nylon. One of skill in the art will appreciate that a variety of materials can be used in the construction of the device. A certain prototype embodiment features the components set forth in Table 1 below.

TABLE 1

| Component | Manufacturer | Order Code | Price & Quantity (Per Device) |
|---|---|---|---|
| Swiveling tip 6 | McMaster-Carr | 8955A12 | $5.32 × (1pc) |
| Adjustment screw 7 5⁄16"-18 Thread, 1¾" Long, Zn plated | McMaster-Carr | 92865A589 | $0.21 × (1pc) Sold in pack of 50 |
| Adjustment nut 8 5⁄16"-18 Thread Zn plated | McMaster-Carr | 95462A030 | $0.07 × (1pc) Sold in pack of 100 |
| Light 25 Pre-wired 5 mm LED White DC3-6 V Clear Lens | Uxcell (or equivalent) | a18050900ux0121 | $0.85 × (1pc) Sold in pack of 10 |
| Button Battery Holder Coin Cell Battery Holder w/ Switch CR2032 | Alinan (or equivalent) | B09KTXB87B | $1.24 × (1pc) Sold in pack of 5 |
| 3 Volt Lithium Coin Cell Battery CR2032 | Amazon Basics (or equivalent) | B0787K2XWZ | $1.38 × (1pc) Sold in pack of 4 |
| Fastening strap 5 Tie w/ Buckle 6" overall length | McMaster-Carr | 3955T88 | $1.40 × (1pc) | case, support arm 2 is placed around the back of the patient's neck on the side of the lacerated artery. The teeth in the complimentary portions of the T-channel in occluding arm lower limb 12 and support arm upper limb 20 can then be engaged and occluding arm 1 and support arm 2 moved together until the occluding head 4 is in the desired place on the wound. At this point the user can let go of the device and the teeth will keep it in place. Next, fastening strap 5 is wrapped around both the occluding arm lower limb 12 and support arm upper limb 20 to secure the device for transit. If the occluding arm 1 has been depressed to occlude the hemorrhage, fine adjustment knob 3 may be used to fine tune placement of occluding head 4 on the wound. Fine adjustment knob 3 can be used to continue to increase pressure while the patient is in transit if extra pressure is needed to maintain occlusion. With this embodiment of the device applied, medical personnel still can intubate the patient, or they can perform a field surgical procedure such as a tracheotomy or cricothyrotomy.

To use the device as an intubation-assist device, support arm insert 22 is removed from laryngoscope blade 23 as shown in FIG. 4. Light 25 is activated and laryngoscope blade 23 is then employed to insert an endotracheal tube into the patient's tracheal via the oropharynx. In some embodiments, a contact switch is incorporated into support arm upper limb 20 so that light 25 is activated automatically when support arm insert is removed. The device is removed from the oropharynx after intubation and the endotracheal tube is secured to the patient. With intubation complete, support arm insert 22 may be reapplied to the laryngoscope blade 23 to utilize the device for the purpose of carotid occlusion, as described above.

The majority of device components in prototypes of certain embodiments have been 3D printed using ABS plastic. These same components may also be injection Assembly of the occlusion arm 1 is illustrated in FIG. 8. The device is assembled by first attaching the fine adjustment knob 3 to the head of adjustment screw 7 with adhesive. Next, with the same adhesive, combine the adjustment nut 8 into the recess 9 of the occlusion arm. Then the applicator head 4 is secured to the off the shelf swiveling tip 6 with adhesive. In preferred embodiments, a high-durability adhesive such as Loctite® is used to secure the swiveling tip and applicator head sub-assembly to the screw to minimize risk of disassembly while using the device.

After the adhesive has dried in each sub-assembly, the adjustment screw 7 is threaded into adjustment nut 8, then the swiveling tip 6 is threaded onto the end of the screw. Loctite is used to secure the swiveling tip 6 and applicator head 4 sub-assembly to the screw so there is no risk of disassembly while using the device.

For dual-use embodiments featuring the laryngoscope blade, a battery holder is adhered to the inner face of the upper limb of support arm 20. The wire leads are routed through a channel in the upper limb of support arm 20 into a recessed channel in the T-slot. With a small amount of adhesive, the leads are held in position so they do not interfere with the sliding of the occlusion arm 1 relative to support arm 2. Then the wire leads of the LED are cut to length and soldered to the appropriate battery leads. After the LED is properly powered, it is pushed into place in the support arm and fixed with adhesive.

Once the occluding arm 1 subassembly is complete, fastening strap 5 is adhered to the support with adhesive. The occluding arm 1 slides into the T-slot incorporated into support arm upper limb 20. Next, laryngoscope blade 23 is inserted into channel 26 of detachable neck support 22 so that the cylindrical tip 24 of laryngoscope blade 23 locks into locking cavity 27.

An alternate embodiment features an inflatable occluding head 4 in the form of an air bladders that is attached to a cervical collar, as shown in FIG. 11. The interior of the cervical collar would be lined with one side of hook-and-loop fastening material, and the inflatable occluding head 4 would have a complimentary strip of material. This would permit flexibility in positioning the occluding head. In such an embodiment, the occluding head would feature an attachment fitting for an inflation pump. Once the occluding head is positioned, the inflation pump would be used to inflate the occluding head to until bleeding was occluded.

Embodiments of the device were subjected to a total of forty-two perfusion experiments using two different cadavers (1 male and 1 female). The experimental setup used in these experiments to simulate a live individual using a blood vessel pumping system similar to heart bypass surgeries and simulated blood is described in: Carey J N, Leland H A, Minneti M, Demetriades D and Taluing P Perfused fresh cadavers: method for application to surgical simulation. Am J. Surg, 2015, Vol 210(1), pp 179-187, and Russin J J, Mack W J, Carey J N, Minneti M, Giannotta S L Simulation of a high-flow extracranial-intracranial bypass using a radial artery graph in a novel fresh tissue model. Operative NeuroSurgery, 2012, December 71 (2 suppl operative) pp. 315319.

Figure 13:
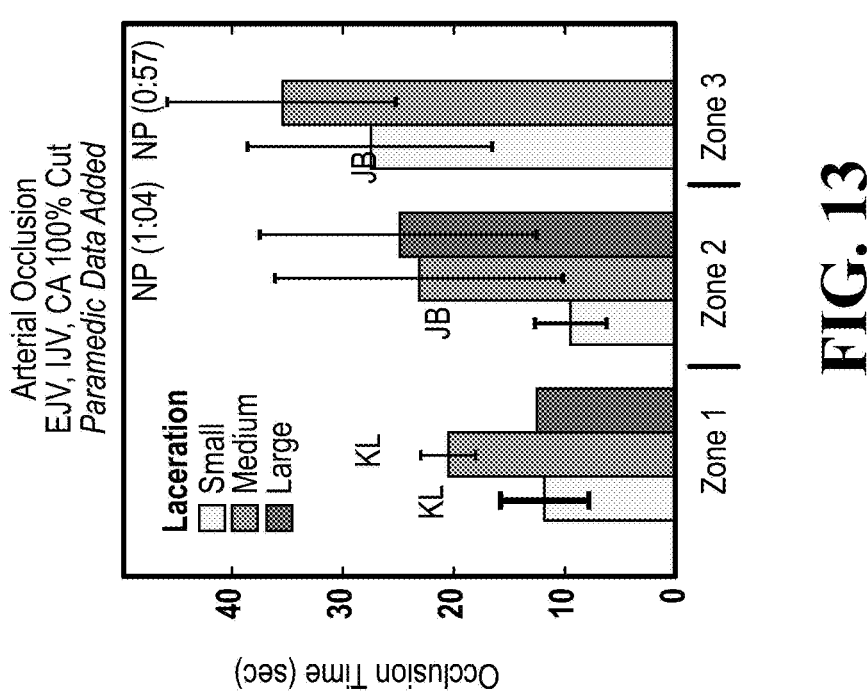
FIG. 13 provides data illustrating cadaverial application testing data.
Figure 12:
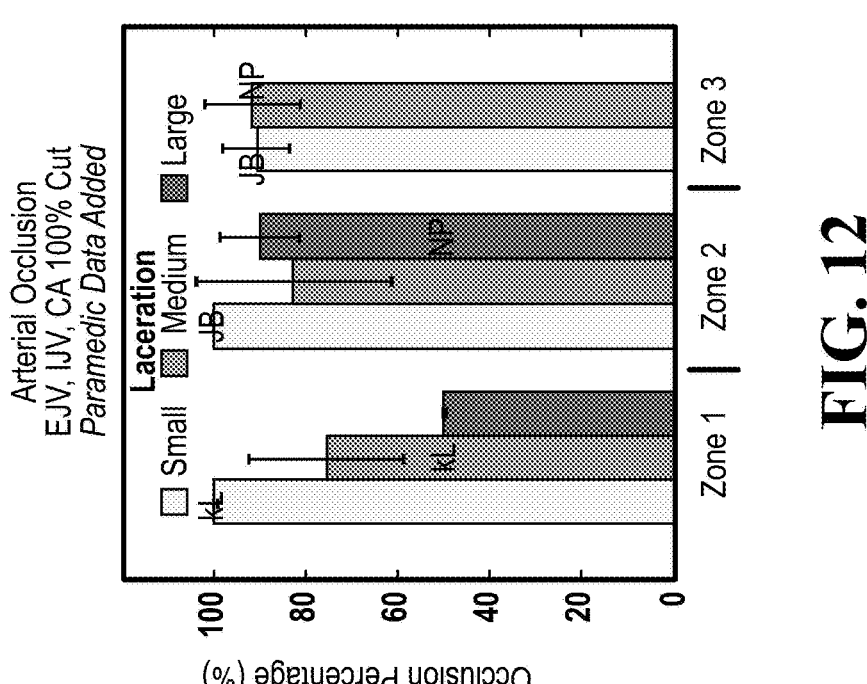
FIG. 12 provides data illustrating cadaverial application testing data.

The results of these tests with the device embodiments using the setup described in the articles above are summarized in FIGS. 12 and 13. FIG. 12 shows the occlusion percentage for small medium and large lacerations for all three zones. A 100% occlusion means that all blood flow from the laceration was stopped. In these tests, the interior and exterior jugular veins as well as the carotid artery were 100% cut. The laceration refers to the size of the soft tissue cut on the tissue above the veins and artery. Small, medium and large lacerations refer to sizes of 1.8-2.5 cm, 3.2-3.9 cm and 4.2-5.5 cm, respectively. The results in the bar charts were obtained from a physician. Also shown are the results from individuals with EMT Basic certification indicated by initials. These individuals had no specific training regarding this device or injury prior to the perfusion experiments. FIG. 13 shows experimental data from the same experiment as that shown in FIG. 12. However, the graph indicates the time required to attain the results on the previous graph.

Additionally, a component of the preferred embodiment is to use the C-Fill component for junctional occlusion. This is done by removing the C-Fill from the occlusion arm and attaching the preset straps to the designated regions. By adjusting the pull straps, the bottom face of the C-Fill can be secured into position.

The embodiments above are intended to be used with hemostatic gauze for medium and large lacerations. As these embodiments reflect an emergent care device in the field under combat conditions, it is expected that these embodiments will be used in conjunction with a variety of field-expedient materials (e.g. combat shoelaces which can be used to hold the device in position while applied in the Zone 1 region of the neck.)

The embodiments above are described herein primarily in the context of a penetrating neck injury. However, these embodiments are also applicable to the following contexts.

Junctional Device—Femoral Triangle (Groin)

One additional use of the embodiments described herein is for junctional compression of the femoral triangle, otherwise known as the groin. To accomplish this, the insert arm piece of the device is first applied to the femoral triangle area of the patient with the convex side placed against the skin or clothing. Next, the insert piece is secured to the patient by attaching a piece of webbing, shoelace, cord, or other cord-like apparatus (hereto referred to as "Cord") to each end of the insert arm, thereby making a tourniquet compression device. The Cord may be tightened to compress the area more. The Cord may be placed around legs or waist to further position or secure the device for this intended use. The device may be used in conjunction with the insert piece for this intended use. The device or insert may be used in conjunction with or secured to rescue equipment, body armor, clothing, gear, or other accoutrement to further enhance positioning or securing of the device.

Junctional Device—Clavicular (Lower Neck)

Another application of the embodiments is for junctional compression of the clavicular or sternoclavicular joint area of the lower neck, otherwise known as the collar bone. To accomplish this, the insert arm piece of the device is first applied to the clavicular or sternoclavicular joint area of the patient with the convex side placed against the skin or clothing. Next, the insert piece is secured to the patient by attaching a Cord to each end of the insert arm, thereby making a tourniquet compression device. The Cord may be tightened to compress the area more. The Cord may be placed around arms or chest to further position or secure the device for this intended use. The device may be used in conjunction with the insert piece for this intended use. The device or insert may be used in conjunction with or secured to cervical collar, rescue equipment, body armor, clothing, gear, or other accoutrement to further enhance positioning or securing of the device.

Junctional Device—Axilla

An additional use of the device is for junctional compression of the axillary area, otherwise known as the armpit. To accomplish this, the insert arm piece of the device is first applied to the axillary area of the patient with the convex side placed against the skin or clothing. Next, the insert piece is secured to the patient by attaching a Cord to each end of the insert arm, thereby making a tourniquet compression device. The Cord may be tightened to compress the area more. The Cord may be placed around arms or chest to further position or secure the device for this intended use. The device may be used in conjunction with the insert piece for this intended use. The device or insert may be used in conjunction with or secured to rescue equipment, body armor, clothing, gear, or other accoutrement to further enhance positioning or securing of the device.

Large Defects of Neck

An additional use of embodiments of the device is for compression of large defects or wounds of the neck. To accomplish this, the device is readied in its routine compression configuration. Then, additional wound dressing (e.g., gauze, combat gauze, packing, ABD pad, clothing) is placed against the defect. The device is placed as described and illustrated in FIG. 10 against the patient and secured upon the aforementioned wound dressing, thereby acting as large wound dressing secure device. Cord may be placed around arms or chest to further position or secure the device for this intended use. The device may be used in conjunction with the insert piece for this intended use. The device or insert may be used in conjunction with or secured to cervical collar, rescue equipment, body armor, clothing, gear, or other accoutrement to further enhance positioning or securing of the device.

Abdominal or Truncal Compression

An additional use of the device is for compression of the abdomen or lower trunk region. To accomplish this, the insert arm piece of the ARC device is applied to the area of the patient with the convex side placed against the skin or clothing. Next, the insert piece is secured to the patient by attaching a Cord to each end of the insert arm, thereby making a compression device. The Cord may be tightened to compress the area more. The Cord may be placed around legs or waist to further position or secure the device in this context. The device or insert may be used in conjunction with or secured to rescue equipment, body armor, clothing, gear, or other accoutrement to further enhance positioning or securing of the device.

Chest or Thoracic Compression

An additional use of the device is for compression of the chest or thoracic region. To accomplish this, the insert arm piece of the device is applied to the area of the patient with the convex side placed against the skin or clothing. Next, the insert piece is secured to the patient by attaching a Cord to each end of the insert arm, thereby making a compression device. The Cord may be tightened to compress the area more. The Cord may be placed around arms or chest to further position or secure the device for this intended use. The device or insert may be used in conjunction with or secured to rescue equipment, body armor, clothing, gear, or other accoutrement to further enhance positioning or securing of the device.

Extremity Tourniquet

An additional use of the device is for compression of an extremity. To accomplish this, the insert arm piece of the device is first applied to the area of the extremity above the injury with the convex side placed against the skin or clothing. Next, the insert piece is secured to the patient by attaching a Cord to each end of the insert arm, thereby making a tourniquet compression device. The Cord may be tightened to compress the area more. The device or insert may be used in conjunction with or secured to rescue equipment, body armor, clothing, gear, or other accoutrement to further enhance positioning or securing of the device.

Head Wound Compression

An additional use of the device is for compression of a head wound or to secure wound dressings. To accomplish this, the insert arm piece of the device is first applied to the area of the head above the injury with the convex or concave side placed against the scalp. Next, the piece is secured to a cervical collar, body armor, or other accoutrement by attaching a Cord to each end of the insert arm, thereby making a compression device. The Cord may be tightened to compress the area more.

What is claimed is:

1. An apparatus for occluding arterial blood flow from a neck wound of a patient, comprising:

an occluding arm comprising:

a occluding arm first limb comprising a straight first elongated member;

a straight occluding arm second limb extending from one end of the occluding arm first limb at an encounter angle;

whereas the occluding arm second limb comprises an adjustable occlusion applicator, the adjustable occlusion applicator comprising:

a swiveling occlusion head comprising a tapered cylinder comprising a top that is flat or concave, and adapted to apply pressure to a first side of the patient's neck in the vicinity of the neck wound;

a support arm comprising:

a support arm first limb, comprising a straight second elongated member; and a support arm second limb extending from one end of the support arm first limb comprising a curved member adapted to apply pressure to a second side of a patient's neck approximately opposite from the neck wound;

wherein the support arm second limb further comprises a laryngoscope blade disposed within a channel disposed within the curved member, such that the curved member is adapted to be detachable from the laryngoscope blade; and wherein the first elongated member and the second elongated member are adapted to engage and translate linearly relative to each other, such that the distance between the occlusion head and the curved member is reduced, whereby the occlusion head and curved member each exert an opposing collinear resultant force through a blood vessel in the patient's neck.

2. The apparatus of claim 1, wherein the encounter angle is from 15-25 degrees.

3. The apparatus of claim 1, wherein the encounter angle is 20 degrees.

4. The apparatus of claim 1, wherein the pressure exerted by the occlusion head is manually adjustable using an occlusion head adjustment knob connected to the occlusion head.

5. The apparatus of claim 1, wherein the first elongated member comprises:

a first set of ratcheting teeth disposed on either side of a t-shaped rail extending outwardly from a first side of the first elongated member; and wherein the second elongated member comprises:

a second set of ratcheting teeth disposed on either side of a slot disposed on a first side of the second elongated member, and a t-shaped channel disposed in the interior of the second elongated member, the t-shaped channel being adapted to accommodate the t-shaped rail, whereas a gap exists between a top of the t-shaped rail and the corresponding portion of the channel, such that the first set of ratcheting teeth and the second set of ratcheting teeth can be manually engaged and disengaged.

6. The apparatus of claim 1, wherein a lower side of the laryngoscope blade incorporates a light, and wherein the second elongated member further comprises a battery compartment for the light.

* * * * *